United States Patent
Schiller et al.

(10) Patent No.: US 6,546,787 B1
(45) Date of Patent: Apr. 15, 2003

(54) MEANS AND METHOD FOR MODELING AND TREATING SPECIFIC TISSUE STRUCTURES

(75) Inventors: Peter J. Schiller, Coon Rapids, MN (US); Angela K. Drexler, Maplewood, MN (US); David R. Wulfman, Minneapolis, MN (US); Ronald C. McGlennen, Edina, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/276,076

(22) Filed: Mar. 25, 1999

(51) Int. Cl.[7] .................................................. G01N 3/00
(52) U.S. Cl. ............................................ 73/85; 73/781
(58) Field of Search ........................ 73/720, 781, 727, 73/398, 787, 818, 827, 81, 85

(56) References Cited

U.S. PATENT DOCUMENTS

| | | |
|---|---|---|
| 2,959,056 A | 11/1960 | Traite et al. |
| 3,038,465 A | 6/1962 | Allard et al. |
| 3,550,583 A | 12/1970 | Chiku et al. |
| 4,299,230 A | 11/1981 | Kubota |
| 4,456,013 A | 6/1984 | De Rossi et al. |
| 4,548,205 A | 10/1985 | Armeniades et al. |
| 4,722,350 A | 2/1988 | Armeniades et al. |
| 4,722,730 A | 2/1988 | Levy et al. |
| 4,771,782 A | 9/1988 | Millar |
| 4,801,293 A | 1/1989 | Jackson |
| 4,841,984 A | 6/1989 | Armeniades et al. |
| 4,886,070 A | 12/1989 | Demarest |
| 4,919,653 A | 4/1990 | Martinez et al. |
| 4,940,458 A | 7/1990 | Cohn |
| 5,227,730 A | 7/1993 | King et al. |
| 5,279,567 A | 1/1994 | Ciaglia et al. |
| 5,320,101 A | 6/1994 | Faupel et al. |
| 5,396,897 A * | 3/1995 | Jain et al. .................... 128/748 |
| 5,421,821 A | 6/1995 | Janicki et al. |
| 5,454,374 A * | 10/1995 | Omachi ........................ 73/708 |
| 5,487,308 A * | 1/1996 | Demarest et al. ............. 73/827 |
| 5,517,846 A | 5/1996 | Caggiani |
| 5,520,650 A | 5/1996 | Zadini et al. |
| 5,546,041 A | 8/1996 | Szajda |
| 5,715,827 A | 2/1998 | Corl et al. |
| 5,807,265 A | 9/1998 | Itoigawa et al. |
| 6,068,622 A * | 5/2000 | Sater et al. .................. 604/254 |
| 6,176,856 B1 * | 1/2001 | Jandak et al. ................. 606/29 |

OTHER PUBLICATIONS

H. Ragde, M.D., et al., Use of Transrectal Ultrasound in Transperineal Iodine Seeding for Prostate Cancer: Methodology, *Journal of Endourology*, vol. 3, No. 2, 1989, pp. 209–218.

J. L. Friedland, M.D., et al., Problems with Rigid Seed Strand Lodging During Prostate Implantation: A Proposed Mechanism and Solution, *Medical Dosimetry*, vol. 22, No. 1, 1997, pp. 17–21.

Tyler M. Lembcke, Trans–Rectal Ultrasound–Guided Trans– Perineal Implants of the Prostate Using I–125 and Pd–103, Chapter 21, Equipment and Supplies, (physics@execpc.com; "http://www.execpc.com/physics/prostate"; available on the internet on Oct. 6, 1997.

(List continued on next page.)

*Primary Examiner*—Max Noori
(74) *Attorney, Agent, or Firm*—Mueting Raasch & Gebhardt

(57) ABSTRACT

Diagnostic imaging methods, methods of detecting the margin of tissue structures and bioresponsive needle systems are disclosed. The methods rely on the use of strain signals provided by a strain gage mounted on the wall of one or more needles as the needle or needles are moved through tissue. The systems employ a strain gage mounted on the wall of the needle and a strain monitor providing feedback to a user.

18 Claims, 6 Drawing Sheets

OTHER PUBLICATIONS

M. Palken, M.D., Comparison of Ultrasound and Digital Rectal Findings with Surgical Specimens: Implications for Staging and Treatment.

Massachusetts Institute of Technology Researchers, 11/21 #02 MIT Researchers Develop a Smart Needle to Help Diagnose Cancerous Tumors, ("http://hightech.cplaza.ne.jp/1996/1996 1 1 1 8/1996 1 121/02/emain.htm"); available on the internet in Aug. 1996.

Gardnfry, Microsensors: Principles and Applications, Wiley, NY, 1994, pp. 78–194.

Dr. Robert Mah (NASA Responsible Official), Robotic Neurosurgery Objectives, *Smart Systems Home Page*,, ("http://ssg.arc.nasa.gov/projects/neurosurgery/objective.html"); available on the internet in Nov. 1998.

C. C. Ling, PhD., et al., Dose Inhomogeneity in Interstitial Implants Using I–125 Seeds, *Radiation Oncology Biol. Phys.*, vol. 5, 1979, pp. 419–425.

Hiemenz, et al., Development of the Force–Feedback Model for an Epidural Needle Insertion Simulator, *Medicine Meets Virtual Reality*, IOS Press and Ohmaha, 1998, pp. 272–277.

Brett, et al., Simulation of Resistance Forces Acting on Surgical Needles, *Proc Inst Mech Engrs* vol. 211 Part H, H02696 copyright IMechE 199, pp. 335–348.

* cited by examiner

MEANS AND METHOD FOR MODELING AND TREATING SPECIFIC TISSUE STRUCTURES

FIELD OF THE INVENTION

The present invention generally relates to surgical procedures and, more particularly, provides an improved system for modeling tissue structure. The system of the invention can be used in locating specific tissue structures for both diagnostic and therapeutic purposes, e.g., in pinpointing the location of a tumor during brachytherapy, needle biopsy or the like.

BACKGROUND OF THE INVENTION

An increasing number of minimally invasive surgical procedures are being developed to reduce the need for major surgery. One problem encountered in many minimally invasive procedures is an inability to see the area of interest within a patient's body. This has been addressed in a number of different ways. For procedures which are performed within a channel or cavity within the patient's body, a camera or other remote visualization tool can be used. This tends to work best in large cavities (e.g., in thoracic or abdominal procedures) or in larger non-vascular conduits (e.g., in procedures involving the digestive tract or fallopian tubes).

Certain advancements are being made in visualizing tissue in real time in other procedures as well. For example, ultrasound catheters are gaining acceptance for use in angioplasty and other vascular procedures while a great deal of research effort is being devoted to developing real-time magnetic resonance imaging. For most other procedures, the surgeon's options are limited to fluoroscopy. The shortcomings of currently available visualization technologies are particularly acute in procedures involving tissue structures within larger tissue masses. For example, current techniques make it difficult for a physician to pinpoint a suspected tumor in the breast during the course of a needle biopsy. In many instances, such tumors are difficult to visualize using fluoroscopy and the physician often must rely on an earlier MRI or CT image as a rough guide in conducting the procedure.

Another procedure that is limited by currently available real-time visualization techniques is interstitial brachytherapy. In interstitial brachytherapy, a radioactive source is implanted directly into and/or immediately around a tissue structure to be irradiated. For example, in treating prostate cancer, radioactive "seeds," which may comprise small spheres of a radioactive isotope, are deposited within and around the prostate organ. While such concentration of the radiation tends to minimize collateral tissue damage, it can be quite difficult to precisely position the radioactive seeds within the tumor because there is no accurate means to visualize the area of interest during the procedure. Instead, a surgeon must rely on a previous MRI, CT or ultrasound image.

Certain highly specialized approaches have been developed to provide real-time feedback during the course of select procedures. For example, a number of techniques have been developed to carefully position an epidural needle within the epidural space of a spinal column. Each of these techniques relies on the principle that the pressure in the epidural space is lower than that in the patient's tissue or within the arachanoid membrane surrounding the spinal cord itself. When this drop in pressure is detected, a signal is given to the physician or, in some cases, further advancement of the needle is prohibited. Examples of such techniques include those set forth in U.S. Pat. No. 5,517,846 (Caggiani), U.S. Pat. No. 4,940,458 (Conh) and U.S. Pat. No. 4,919,653 (Martinez et al.). While these fluid pressure monitoring techniques work well in placing epidural needles in the epidural space, the utility of this technique in other tissue-related applications is rather limited.

A variety of remote fluid pressure assessing devices are also known in the art. Most of these devices utilize sealed catheters or the like which utilize a pressure transducer. The pressure transducer monitors the pressure differential between the fluid within the lumen of the catheter and the fluid external to the catheter. Examples of such structures are shown in U.S. Pat. No. 5,807,265 (Itoigawa et al.), U.S. Pat. No. 4,456,013 (De Rossi et al.) and U.S. Pat. No. 3,550,583 (Chiku et al.), among others. While such remote fluid pressure sensing devices can be useful in monitoring pulse rate, blood pressure or the like, such fluid pressure measuring systems have limited benefits in procedures focusing on tissue structures.

In light of the above, it would be advantageous in many circumstances to have an alternative means for modeling or visualizing a body structure. It would be particularly advantageous to have such a technique which would allow a physician to better visualize a tissue structure within a larger body of tissue on a real-time basis.

SUMMARY OF THE INVENTION

The present invention provides a diagnostic imaging method, a method of detecting a margin of a tissue structure of interest, and a bioresponsive needle system. In accordance with one preferred diagnostic imaging method, the operator is provided with at least one needle having a wall and a distal tip, with a strain gage being connected to the needle wall at two spaced-apart locations. The strain gage generates a strain signal in response to strain on the wall of the needle. The distal tip of this needle is inserted into a patient's tissue and the needle is advanced distally into the tissue along a first needle path. The strain signal generated during this distal advancement of the needle along the first needle path is monitored. The distal tip of the same needle (or, alternatively, a separate needle having the same structure) is inserted into a patient's tissue and the needle is advanced distally into the tissue along a second needle path. The strain signal generated during the distal advancement of the needle along the second needle path is monitored. The strain signals generated along the first and second needle paths are correlated with at least two locations along a margin of a tissue structure.

In a further refinement of this technique, the first and second needle paths can follow a prescribed relationship with respect to one another such that the relative positions of the two locations along the margin can be determined. By using a plurality of such needles, a three-dimensional image of the tissue structure can be formed.

An alternative method of the invention permits the detection of at least one margin of a tissue structure of interest, e.g., the margins of a prostate tumor. In accordance with this method, the operator is provided with a needle having a wall and a distal tip, with a strain gage being connected to the needle wall at two spaced-apart locations. The strain gage generates a strain signal in response to strain on the wall of the needle. The distal tip of the needle is inserted into tide patient's tissue and the needle is advanced distally into the tissue. The strain signal generated during the distal advancement of the needle is monitored and the strain signal is analyzed to detect the margin of the tissue structure. This can be accomplished, for example, by positioning the strain gage distally of a proximal end of the needle such that at least a portion of the strain gage is positioned within the patient's tissue during at least part of the distal advancement of the needle. If so desired, analyzing the strain signal may include identifying at least one amplitude change, e.g., a sharp discontinuity, in a signal response curve and correlating that change with a margin of the tissue structure.

One bioresponsive needle system of the invention includes an elongated needle adapted to be inserted into a patient's tissue. Optimally, this needle has a lumen and a wall. A strain gage is connected to the needle wall at two spaced-apart locations, with the strain gage generating a strain signal in response to strain on the wall of the needle. A strain monitor is operatively connected to the needle and is adapted to provide a user with feedback regarding the strain on the needle wall. In one particularly useful embodiment, the needle has a proximal hub, a distal tip and a body extending between the proximal hub and the distal tip. A distal length of the body of this needle is adapted to be inserted into a patient's tissue, with the strain gage being positioned along said distal length of the body of the needle. If so desired, the needle system may further comprise a motor connected to the needle proximally of a distal end thereof. Depending on the intended application, the motor may advance the needle distally at a constant rate or by applying a constant force.

DETAILED DESCRIPTION OF THE PREFERRED EMBODIMENTS

Figure 1:
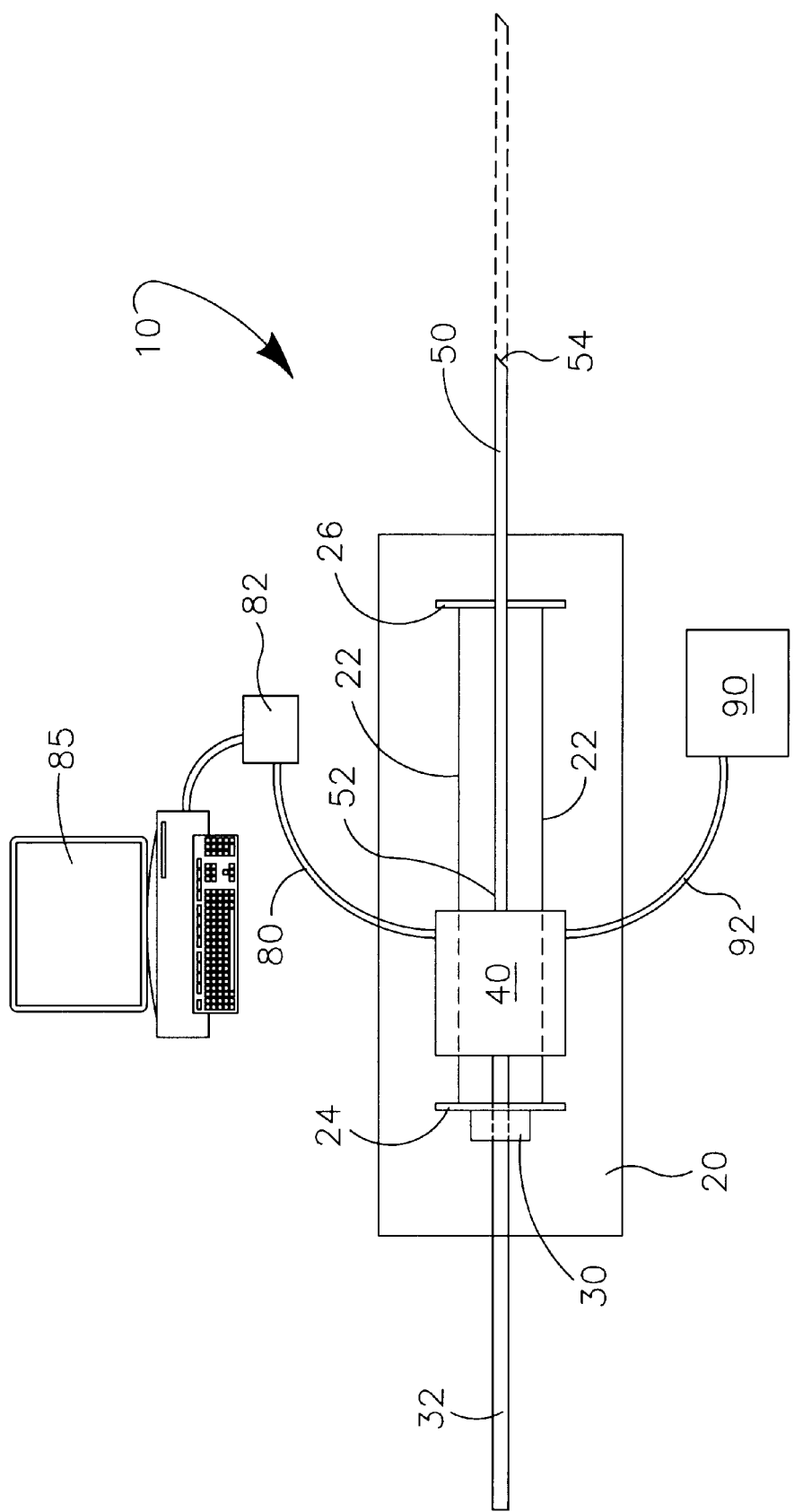
FIG. 1 is a schematic overview of a bioresponsive needle system in accordance with one embodiment of the invention.

FIG. 1 is a schematic overview of a needle system 10 in accordance with one suitable embodiment of the invention. In this embodiment, the needle 50 is supported by an automated support structure. The support structure generally includes a platform 20 having a pair of generally parallel, spaced-apart rails 22 extending from a rear stop plate 24 to a front stop plate 26. A mounting block 40 is adapted to slide along these rails 22, with the rear stop plate 24 defining the maximum travel rearwardly (to the left in FIG. 1) of the block 40 while the front stop plate 26 defines the forward limit of the range of motion. This range of motion is suggested in phantom lines in FIG. 1.

If so desired, the mounting block 40 can be moved manually along the pair of rails 22 to move the needle 50 back and forth. In a preferred embodiment, though, the needle system 10 further includes a motor 30 for controlling motion of the mounting block. Any suitable motor can be used, but it is preferred that the motor allow relatively precise control over the movement of the mounting block 40 with respect to the platform 20. In the illustrated embodiment, the motor 30 is an electronically controllable stepper motor which is engaged to a screw-threaded drive shaft 32. By rotating an internally threaded cuff or worm gear (not shown) of the motor, the drive screw 32 can be advanced and retracted with a minimum of backlash.

In an alternative configuration (not shown), a different type of motor and drive connection is utilized. A brush DC motor is connected to a drum by means of a pulley, or the like. A flexible push rod is wound about the drum. The motor may advance the needle by unwinding the push rod from the drum or retract the needle by winding the push rod onto the drum. While this mechanism may be less precise, it is likely to be more compact and may be enclosed in a simple housing to reduce the risk of contamination.

A communication cable 80 may extend from the mounting block 40 to a signal processor 85. As explained in more detail below, the needle system of the invention can be used to monitor a strain signal generated during advancement of the needle 50 within a patient's tissue. The communication cable 80 is useful in delivering this strain signal to a signal processor 85. The following detailed discussion focuses on the use of an electrical strain signal, in which case the communication cable is typified as a pair or bundle of electrical wires. It is contemplated, though, that the strain signal can take other forms, such as an optical or digital signal and the nature of the communication cable 80 should be appropriately matched to the type of strain signal being generated.

The signal processor 85 can take any desired form, depending on the nature of the strain signal generated and the manner in which that signal is to be monitored and/or otherwise used. In FIG. 1, the signal processor 85 is typified as a programmable computer. As discussed below, this computer can also be used to control the operation of the motor 30, to display a graphical representation of the data gleaned from the strain signal, or any of a wide variety of other functions.

FIG. 1 also illustrates an optional therapeutic agent supply 90 connected to the mounting block 40 by means of a delivery conduit 92. The nature of this therapeutic agent supply and the delivery conduit, as well as the manner in which this delivery conduit is ultimately connected to the needle 50, will vary depending on the nature of the therapeutic agent being delivered. For example, delivering a drug in a parenteral solution may use a syringe and catheter while delivery of radioactive seeds during interstitial brachytherapy would require the use of a different set of specialized delivery tools. In certain operations, e.g., a needle biopsy procedure, there may be no need to deliver any therapeutic agent to the patient. In such circumstances, the therapeutic supply 90 and delivery conduit 92 can simply be omitted from the needle system 10.

The needle 50 has a proximal end 52 which may be operatively connected to the mounting block 40 and a distal tip 54 which desirably extends distally beyond the forward end of the platform 20. The proximal end 52 may be connected to the mounting block in any desired fashion. If the needle has a lumen through which a therapeutic agent or the like is to be delivered, the mounting block may have fluid delivery conduits (not shown) adapted to communicate a therapeutic fluid from the supply 90 into the lumen of the needle. As discussed more fully below, the strain signal may be communicated from the strain gage 60 proximally along the length of the needle using at least one, and preferably two more leads 64 and 66. The connection between the proximal end 52 of the needle and the mounting block 40 desirably facilitates the easy connection of these leads 64 and 66 to the communication cable 80 to ensure a strong, reliable connection therebetween.

Figure 2:
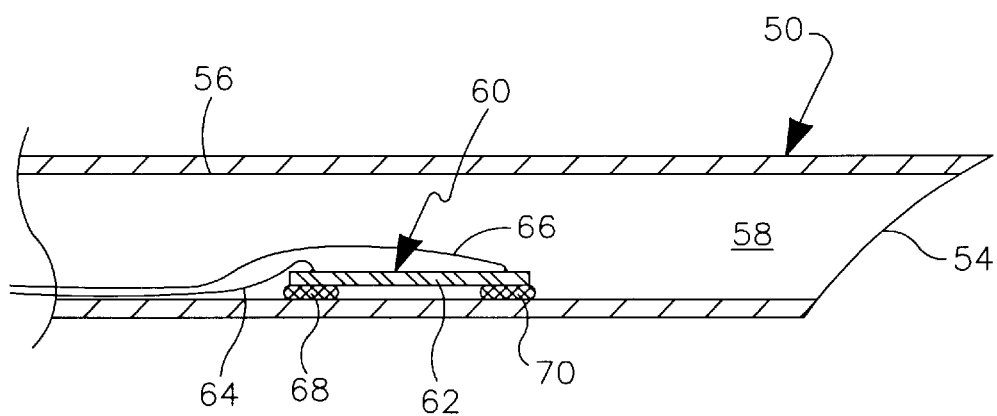
FIG. 2 is a schematic cross-sectional view of a distal portion of one embodiment of a needle of the invention.

FIG. 2 is a cross-sectional isolation view of a distal portion of one useful embodiment of a needle 50. The distal tip 54 desirably defines a leading edge which is sufficiently sharp to penetrate a patient's tissue without undue trauma as the needle is advanced therethrough. The needle 50 of FIG. 2 is generally tubular in construction having a relatively thin wall 56 which defines therein a generally cylindrical lumen 58.

A strain gage 60 is carried by the needle. In the embodiment of FIG. 2, the strain gage 60 has a piezoresistive substrate 62 carried within the lumen 58 of the needle. This substrate 62 is desirably connected to the interior surface of the wall 56 of the needle at two locations spaced along the length of the wall. In FIG. 2, this is typified as being two separate adhesive connections, namely a bead of a suitable biocompatible adhesive defining a proximal connection 68 and a separate bead of a similar adhesive defining a distal connection 70. Between these proximal and distal connections 68, 70, the substrate is relatively free to move with respect to the wall 56 of the needle.

FIG. 2 is intended to schematically illustrate that the substrate 62 of the strain gage 60 is connected to the wall 56 of the needle at a minimum of two spaced-apart locations. As discussed below, the strain gage is intended to measure the strain (e.g., the axial shortening or elongation) of the needle wall. The substrate 62 can just as easily be connected to the wall 56 of the needle by a single adhesive or other bond that extends between two spaced-apart locations on the needle wall. It is sufficient that the adhesive, however applied, serves to induce compression or elongation of the substrate 62 proportionate to the displacement of two or more spaced-apart locations along the needle wall.

A proximal electrical lead 64 may be electrically connected to the piezoresistive substrate 62 adjacent a proximal end thereof. In FIG. 2, this is typified as being positioned vertically above the proximal adhesive connection 68 to the needle wall, but this is not necessary. A distal electrical lead 66 may be electrically connected to the substrate 62 adjacent a distal end thereof. Again, this is typified in FIG. 2 as being positioned above the distal adhesive connection 70 between the substrate and the needle wall. The proximal and distal leads 64, 66 can be connected to the piezoresistive substrate in any of a variety of known fashions, e.g., by a suitable metallic solder.

The operation of piezoresistive strain gages is relatively well documented and need not be discussed in any great detail here. Briefly, though, the piezoresistive substrate is typically formed from a semiconductor material, e.g., silicon or gallium-arsenide of the first conductivity type, but thin metal films of platinum, gold, tungsten or the like are also known in the art. The spaced-apart electrical connections of the proximal and distal leads 64, 66 to the substrate permit an electric current to flow from one contact to the other. In one mode of operation, a relatively constant voltage can be applied between the proximal lead and the distal lead and the magnitude of the resultant current flow will fluctuate in response to the mechanical force imparted by the needle wall 56 to the substrate 62. Alternatively, the electrical current between the two leads can be maintained at a relatively constant level and the magnitude of the resulting voltage between these two leads will vary with the mechanical stress imparted to the substrate by the needle wall. Other refinements of this basic structure and these modes of operation will be readily apparent to one skilled in the art and are easily found in the relevant literature. For example, a description of piezoresistive devices and their operation may be found in Gardner, Microsensors: Principles and Applications, Wiley, New York (1994), the teachings of which, are incorporated herein by reference. (See, e.g., pp 178–194.)

The electrical leads 64, 66 may communicate with the signal processor 85 in any suitable fashion. Theoretically, at least, the current between the two leads 64, 66 (in the case of a constant voltage system) or the voltage between the two leads (in the case of a constant current system) could be transmitted to the signal processor 85 without a direct electrical connection, e.g., by radio signals or an infrared relay system. It is preferred, though, that the electrical leads 64, 66 simply extend proximally along the entire length of the needle for direct electrical connection to the signal processor, such as through the communication cable 80. If so desired, a dedicated power supply 82 may be interposed along the length of the communication cable 80. This power supply 82 may be electronically controllable by the signal processor 85 to condition the power delivered to the strain gage 60, e.g., by maintaining the power at a constant voltage or at a constant current.

Figure 3:
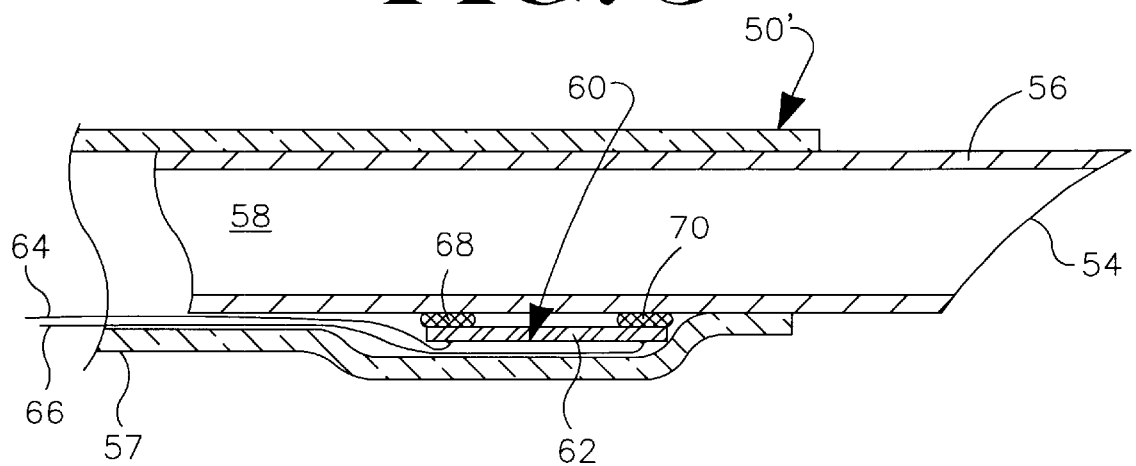
FIG. 3 is a schematic cross-sectional view, similar to FIG. 2, of a distal portion of an alternative needle structure of the invention.

FIG. 3 illustrates an alternative needle 50' in accordance with another embodiment of the invention. Since most of the elements in FIG. 3 serve the same functions as analogous elements shown in FIG. 2, the same reference numbers are used in both figures to refer to like elements.

The primary difference between the needle 50' of FIG. 3 and the needle 50 of FIG. 2 is that the strain gage 60 in FIG. 3 is carried by the exterior surface of the needle wall 56 rather than within the lumen 58, as in FIG. 2. This arrangement may be more appropriate if the therapeutic agent to be delivered through the lumen 58 of the needle 50' is going to be a solid or a particulate matter rather than a fluid which can flow relatively smoothly over the strain gage. If the needle 50' is not to be used to deliver any therapeutic agent, it may be preferable to simply omit the lumen 58. Instead of having a hollow structure such as that shown, the body of such a needle could comprise a solid metal cylinder. By positioning the strain gage 60 on the exterior wall of such a solid cylindrical needle, one should still be able to measure a meaningful strain signal utilizing the strain gage.

If so desired, the strain gage 60 may simply be attached to the exterior surface of the body of the needle, leaving the strain gage exposed. In the embodiment of FIG. 3, though, an external sheath 57 covers the piezoresistive substrate 62 and the leads 64, 66 to help protect the strain gage as the needle passes through a patient's tissue. This sheath 57 can extend only over that distal length of the body of the needle which is adapted to be inserted into the patient's tissue. Alternatively, the sheath can extend approximately all the way to the proximal end 52 of the needle to help protect the leads 64, 66 along the length of the needle. If so desired, the sheath may be formed of a heat shrinkable thermoplastic material to facilitate production. One such material known in the art which will also help reduce friction along the majority of the length of the needle is polytetrafluoroethylene.

Figure 4:
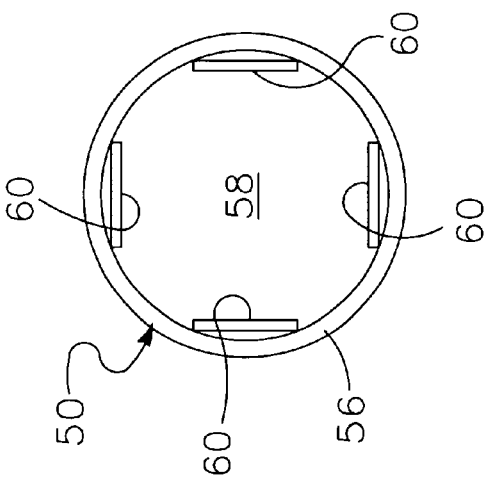
FIG. 4 is a schematic end view of a needle illustrating the positions of a plurality of strain gages within the lumen thereof.

FIGS. 2 and 3 each show a needle structure which utilizes a single strain gage 60. In a preferred embodiment, though, a plurality of strain gages are carried by the needle. FIG. 4 is a schematic end view of one such needle, illustrating four strain gages positioned equiangularly about the internal surface of the needle wall 56. If so desired, each of these strain gages maybe positioned at about the same point along the length of the needle. In certain embodiments, though, it may be advantageous to stagger the positions of the strain gages at different locations along the length of the needle to get a more informative profile of the stress on the wall of the needle at different locations. For example, the upper and lower strain gages can be positioned closer to the distal tip of the needle while the strain gages on the left and right sides of FIG. 4 may be spaced proximally a significant distance behind that distal tip. Other arrangements of multiple strain gages on the needle 50 could also be selected to achieve any particular design objectives.

The position(s) of the strain gage(s) along the length of the needle can affect the nature of the data generated by the strain gage and the ease of use and cost of manufacture of the needle. Positioning the strain gages toward the distal tip 54 of the needle will probably give the-most precise, accurate indication of the nature of the tissue immediately adjacent the distal end of the needle. Unfortunately, this position requires expensive biocompatible packaging of the gage and, signal leads. Positioning the strain gage(s) proximally so they never enter the patient's tissue would both protect the gage(s) and make it easier to reuse the needle for different patients without any undue difficulty in sterilization.

Mounting the strain gages this far proximally from the distal tip of the needle introduces its own technical difficulties, though. The longer length of the needle wall 56 between the distal tip 54 and the strain gage increases the effect of friction on the strain signal. If the strain gage is positioned immediately adjacent the distal end of the needle, the effects of the friction of the needle wall against the tissue through which the needle passes is believed to be negligible. If the strain gage is positioned more proximally, though, the increased surface area of the needle between the strain gage and the distal tip of the needle increases the frictional component of the strain signal. This frictional component is not constant, but instead increases as more of the needle is advanced into the tissue and even this varies with the nature of the tissue through which the body of the needle passes. In order to mitigate these frictional effects on the strain measurement, one may elect to rely on a strain signal which has been differentiated rather than relying on the raw strain signal; such signal differentiation is discussed below in connection with FIGS. 7A–7D.

A greater distance between the distal tip of the needle and the strain gage is also believed to increase the effects on the strain signal of bending moments attributable to urging the needle adjacent its proximal end. To help isolate these effects, pairs of opposed strain gages may be used. In particular, the compressive force on one strain gage is largely offset by a similar tensile force on the other strain gage of the opposed pair. As a result, comparison of the strain signals from the two gages will help isolate the effect of these bending moments and better isolate the strain attributable to axially compressive stress on the needle wall. Thus, it is necessary to balance the reliability, cost and convenience of such proximally positioned strain gages with the enhanced precision and responsiveness associated with positioning the strain gages closer to the distal tip of the needle.

Figure 5:
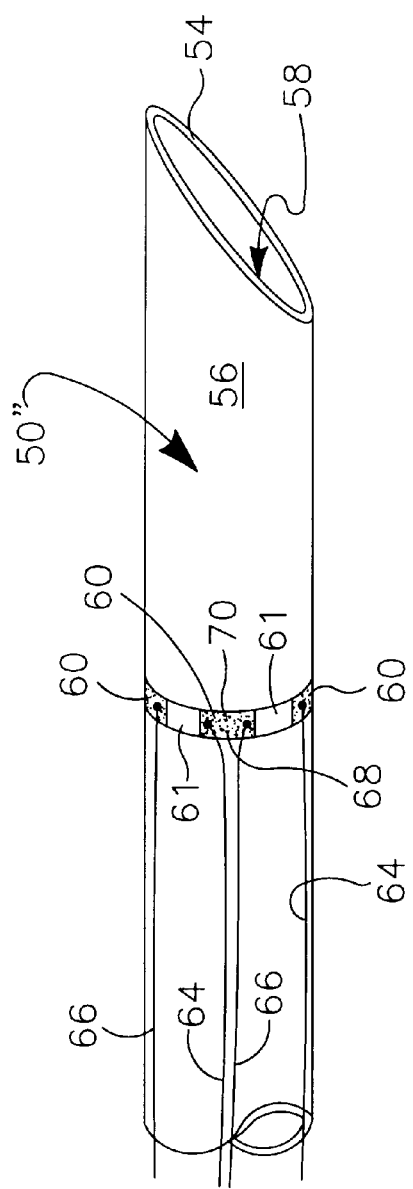
FIG. 5 is a schematic cross-sectional view of another alternative needle design which incorporates a plurality of strain gages into the structure of the wall of the needle.

FIG. 5 illustrates another embodiment of a needle 50'' in accordance with another alternative embodiment of the invention. The needle 50'' does not include any strain gages separately mounted on the interior or exterior surface of the wall 56. Instead, each of the strain gages 60 are incorporated into the structure of the wall 56 itself. Nonetheless, these strain gages 60 are deemed to be connected to the needle, wall at two spaced apart locations 68, 70 and are adapted to provide meaningful feedback regarding the strain along the needle wall at that point. While it may be possible to use a single annular piezoresistive substrate, it is expected that a plurality of independent substrates would instead be used. If so desired, the separate strain gages 60 may be spaced about the circumference of the needle by a series of spacers 61 positioned there between. These spacers may be formed of any suitable material, such as stainless steel. If so desired, both the strain gages 60 and spacers 61 may be formed of silicon or another piezoresistive material to simplify manufacture.

One of the primary advantages of a needle system 10 in accordance with the present invention is the ability of the needle to generate a strain signal which is responsive to the strain placed on the body of the needle 50. This real-time feedback regarding the conditions encountered by the needle as it passes through a patient's tissue can give an operator some meaningful insight into the nature of the tissue through which the needle is passing. This information can, in turn, be used to enable the operator to pinpoint the margins of a tissue structure of interest, such as a tumor which is to be biopsied or treated using interstitial brachytherapy.

In practicing a method of the present invention, one will typically utilize a needle having a wall and a distal tip, with a strain gage being connected to the needle wall at two spaced-apart locations. This strain gage should be adapted to generate a strain signal in response to strain on the wall of the needle. In the following discussion, reference will be made to reference numbers used in FIGS. 1–5 to help clarify the explanation of the method. It should be understood, though, that any other needle which is adapted to deliver a strain signal that can be used in the method of the invention could be used instead and any reference to FIGS. 1–5 is not to be seen as limiting the structure of the needle used in the method.

In one method of the invention, the distal tip of a needle 50 is inserted into a patient's tissue and the needle is advanced distally into that tissue. As the needle passes through the patient's tissue, the needle will encounter resistance to distal movement through the tissue. The resistance of the tissue against the distal tip of the needle will place a compressive stress on the needle, which will typically be pushed from a location adjacent to its proximal end 52. As a result of this compressive stress, the wall 56 of the needle will exhibit a corresponding compressive strain. This change in the dimensions of the needle wall will, in turn, place a compressive stress and resulting strain on the strain gage 60. As a consequence, the strain measured by the strain gage, typified as an electrical strain signal, will give the user some useful feedback regarding the magnitude of the tissue's resistance to further advancement of the needle. As a general rule, a denser tissue mass will tend to exert a greater resistance to advancement of the needle than will a less dense tissue mass. For example, it is usually harder to push the needle through muscle than it is to push the needle through fat.

Other tissue properties can also affect the ease with which the needle can be advanced therethrough. These factors would include the hydration state, the density of vasculature, fibroelasticity, the presence of tissue concretions or other material deposits and variations in microanatomy.

As the needle advances through different tissue structures within a larger tissue mass, the strain on the needle will also vary. As a consequence, when the needle passes from one type of tissue into another type of tissue, this will tend to induce a noticeable change in the strain signal. By correlating the position of the needle and the time at which the change in the strain signal is detected, one can get a feel for the nature of the tissue as a function of distance along the needle's path through the tissue mass.

The needle 50 can either be advanced manually by the operator or b; means of a motor. If the needle is to be manually advanced, the needle system can provide the operator with some visual feedback (e.g., a graph on a computer screen) showing, in real time, the strain on the needle. This, in combination with the operator's perception of the force applied to the needle will give the operator some guidance as to the nature of the underlying tissue structure. Of course, other forms of feedback may be used either instead of or in addition to such a graphical display on a computer screen. For example, the current strain level monitored by the strain gage 60 may be used to generate an audible tone, the volume or pitch of which can be varied in proportion to the measured strain.

It is currently believed that a needle system 10 which utilizes a motor 30 to control advancement of the needle will allow the needle system to give more accurate, detailed information regarding the nature of the tissue through which the needle is passing. If a physician is manually advancing the needle, it can be difficult to accurately deliver information to the signal processor 85 reflecting the force applied to the needle or the position of the needle when a tissue margin is detected. As a consequence, it can be difficult to generate a reliable image of the tissue when the operator advances the needle manually.

If a motor 30 used to advance the needle 50 is controlled by the signal processor 85 or some other component which is connected thereto, the signal processor will be able to correlate the position of the needle with sharp changes in the strain response curve, effectively pinpointing the location of each tissue margin along the needle's path. The fact that the motor can advance the needle distally in a predetermined, repeatable manner tends to reduce anomalies in the strain signal attributable to variations in advancement of the needle which may arise if a physician manually advances the needle.

The motor can be operated in any desired fashion. In some circumstances, the rate at which the needle is advanced and/or the force with which the needle is pushed distally may not be particularly important and merely knowing the length of travel of the needle when a given tissue margin is encountered may be sufficient. In other circumstances, though, a high rate and/or force of advancement may tend to move the tissue sufficiently to affect the data being collected with the needle(s). In order to help isolate one or both of these variables, the motor 30 may advance the needle distally at a constant rate, adjusting the force applied to the needle to maintain that rate. Alternatively, the motor may advance the needle distally by applying a constant force, meaning that the rate at which the needle passes through the tissue will vary depending upon the resistance to advancement of the needle through the tissue.

Figure 6:
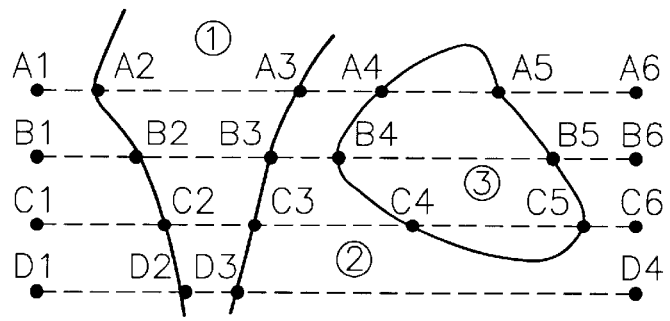
FIG. 6 is a schematic cross section through a large tissue mass having a tissue structure of interest therein.

FIG. 6 schematically illustrates a cross section through an idealized tissue mass which generally includes three distinct tissue regions labeled 1, 2 and 3. In this idealized tissue mass, each tissue region is assumed to be completely homogeneous and tissue region 1 is assumed to be more dense than tissue region 2 while tissue region 3 is assumed to be more dense than either of the other tissue regions. In the case of brachytherapy, these tissue regions 1–3 may be thought of as generally corresponding to muscle, fat and prostate, tissues, respectively. For a lung tumor biopsy, these three regions may instead be thought of as corresponding to muscle, lung and tumor tissues, respectively. This idealized tissue mass does not have any distinct membranes (e.g. skin) at the margins between adjacent tissue regions.

A series of parallel dashed lines extend generally horizontally across FIG. 6, with these lines being labeled A1–A6, B1–B6, C1–C6 and D1–D4. Each of these horizontal lines is intended to represent a different needle path through the tissue.

Figure 6A:
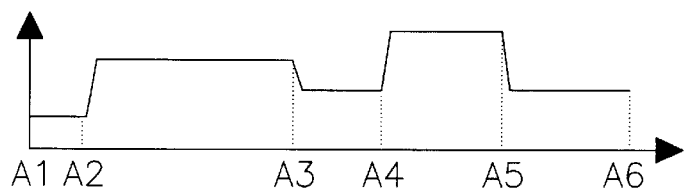
FIG. 6A is a graphic representation of an idealized strain signal generated by a needle of the invention traveling along the path identified as A1–A6 in FIG. 6.

FIG. 6A schematically represents an idealized signal response curve for a needle passing along the needle path A1–A6 in FIG. 6 at a constant penetration rate. FIG. 6A plots the amplitude of the strain signal as a function of distance, assuming the strain gage is operated using a constant bias condition (either a voltage bias or a current bias, as discussed above). The points along the curve of FIG. 6A labeled A1–A6 are intended to correspond to the locations in FIG. 6 identified as A1–A6, e.g., point A3 on FIG. 6A corresponds to a point where the distal tip of the needle encounters location A3 in FIG. 6.

The first part of the curve A1–A6 represents the travel of the needle through the air, prior to entering tissue region 1 at A2. The first part of this curve is quite low (or zero) because there is no substantial compressive stress on the needle until it encounters the tissue. The amplitude of the signal response curve increases fairly sharply once it encounters tissue region 1 at A2, the magnitude being proportional to the strain imparted on the needle to penetrate the tissue. As the needle advances through region 1 (from A2 to A3), the strain signal remains relatively constant as the tissue region is assumed to be homogenous. As the needle enters tissue region 2 at point A3, the strain signal amplitude drops as region 2 is assumed to be less dense, and hence offer less resistance to needle penetration, than tissue region 1. Again, the strain signal will remain fairly constant while the needle is advanced through the ideally homogenized tissue region 2 (from points A3–A4). At A4, the needle enters tissue region 3 and the strain signal again increases abruptly in response to the higher density in that region. The signal remains relatively constant as the needle passes through the tissue region 3 from point A4 to point A5, where the needle extends back into tissue region 2. Between A5 and A6, the strain signal is similar in magnitude to the level between A3 and A4 where it was also passing through tissue region 2.

It has been assumed in this idealized case that friction between the exterior of the needle shaft and the tissue through which the needle is passing has a negligible effect on the signal response curve. This assumption most closely approximates reality when the strain gage is placed adjacent the distal end of the needle and/or for a very low friction needle shaft (e.g., a needle coated with polytetrafluoroethylene or a slippery hydrophilic coating). If the gage is placed toward the proximal end of the needle and friction forces were not negligible, each region of the strain curve in FIG. 6A would have a general upward drift as the friction will increase with greater penetration depth.

Figure 6B:
FIG. 6B is a graphic representation of an idealized strain signal generated by a needle of the invention traveling along the path identified as B1–B6 in FIG. 6.

FIG. 6B schematically represents an idealized signal response curve for a needle passing along the needle path B1–B6 in FIG. 6 at a constant penetration rate. As with FIG. 6A, FIG. 6B plots the amplitude of the strain signal as a function of distance, assuming the strain gage is operated using a constant bias (voltage or current) condition. Similar to the preceding discussion or FIG. 6A, the region B1–B2 corresponds to needle travel through air; the region B2–B3 corresponds to needle penetration through tissue region 1; the region B3–B4 corresponds to needle penetration through tissue Region 2; the region B4–B5 corresponds to needle penetration through tissue Region 3; and the region B4–B6 corresponds to needle penetration through tissue Region 2.

Figure 6C:
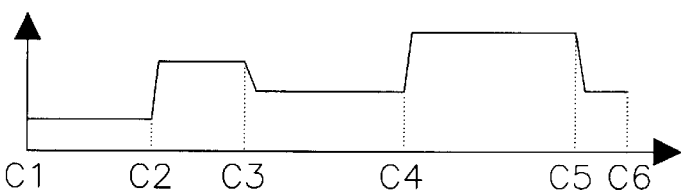
FIG. 6C is a graphic representation of an idealized strain signal generated by a needle of the invention traveling along the path identified as C1–C6 in FIG. 6.

FIG. 6C schematically represents an idealized signal response curve for a needle passing along the needle path C1–C6 in FIG. 6 at a constant penetration rate. As above, the Region C1–C2 corresponds to needle travel through air; C2–C3 corresponds to needle penetration through tissue region 1; C3–C4 corresponds to needle penetration through tissue Region 2; C4–C5 corresponds to needle penetration through tissue region 3; and C5–C6 corresponds to needle penetration through tissue Region 2.

Figure 6D:
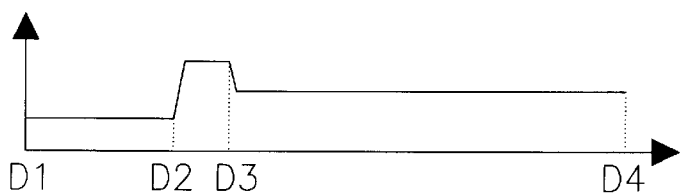
FIG. 6D is a graphic representation of an idealized strain signal generated by a needle of the invention traveling along the path identified as D1–D4 in FIG. 6.
Figure 7A:
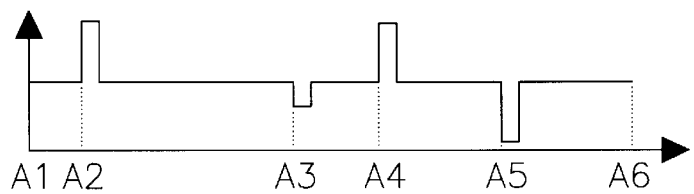
FIG. 7A is a graphic representation of an idealized strain signal generated by differentiating the strain signal of FIG. 6A.
Figure 7B:
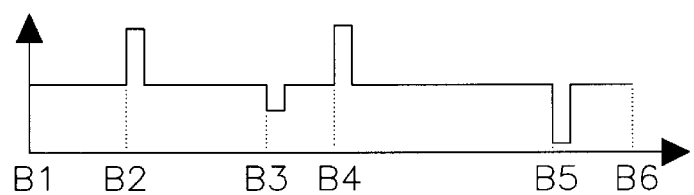
FIG. 7B is a graphic representation of an idealized strain signal generated by differentiating the strain signal of FIG. 6B.
Figure 7C:
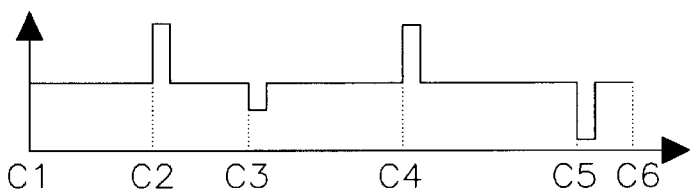
FIG. 7C is a graphic representation of an idealized strain signal generated by differentiating the strain signal of FIG. 6C.
Figure 7D:
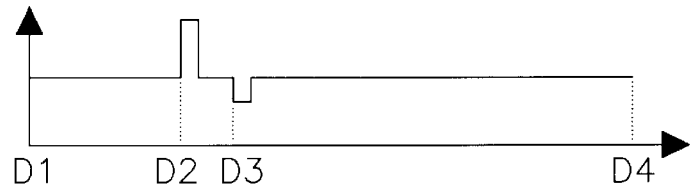
FIG. 7D is a graphic representation of an idealized strain signal generated by differentiating the strain signal of FIG. 6D.

FIG. 6D schematically represents an idealized signal response curve for a needle passing along the needle path D1–D6 in FIG. 6 at a constant penetration rate. Similar to the prior three penetration paths, the needle tip enters tissue 1 at D2 and passes into tissue 2 at D3. However, along the path D1–D4, the needle never penetrates tissue 3 and the strain signal amplitude remains constant between points D3 and D4.

In the idealized example of FIGS. 6A–6B, several simplifying assumptions were made to illustrate the concepts of operation and strain signal interpretation. Depending on the particular application, gage placement on the needle wall, the needle insertion mechanism, and other factors, it may be advantageous to filter or purify the data by processing the raw strain signal.

FIGS. 7A–7D schematically represent the effect of differentiating the signals depicted in FIGS. 6A–6D, respectively. Differentiation is a commonly understood signal processing method that can attenuate undesirable strain signal components, such as those associated with friction along the needle wall. Differentiation also has the advantage of nullifying electronic offsets that may arise from mismatched gage characteristics or amplifier components. Differentiation, as the name implies, involves subtraction of one signal value from a previous signal value to give a difference. The differential is often normalized by the associated difference in time or distance between the two signal components. For example, if S1 is the strain signal magnitude measured at needle position X1, and S2 is the strain signal magnitude measured at needle position X2, then a differential algorithm might generate $D(X2)=(S2-S1)/(X2-X1)$. In this manner, a differential signal processing algorithm amplifies change in the strain signal and attenuates slowly varying or constant strain signal components. For applications where the margins of tissue are most important, the strain signal changes may be most important. A differential signal processing algorithm may be incorporated in the signal amplifier, or more commonly, within the software of the data processing/display computer.

As can be seen by comparing FIGS. 7A–7D with FIGS. 6A–6D, the differentiated strain signal of FIG. 7 has an even sharper change. At each tissue interface, e.g. A1, A3, A4 and A5 in FIG. 7A. This differentiated strain signal can both enhance readability of the curve by an operator and, in some anticipated embodiments, make it easier to automatically detect tissue margins electronically.

The plots of FIGS. 6A–6E may each be thought of as a "1-dimensional" image. In particular, each of these plots comprise a graphical representation of a characteristic of the tissue (resistance to advancement of the needle therethrough) as a function of distance along a given path. While this graphical "image" may not give a physician as much information about the tumor at large as would a traditional two-dimensional "tissue slice" image or a three-dimensional representation from an MRI or CT scan, such one-dimensional plots are very informative about the nature of the tissue along a particular path.

Figure 8:
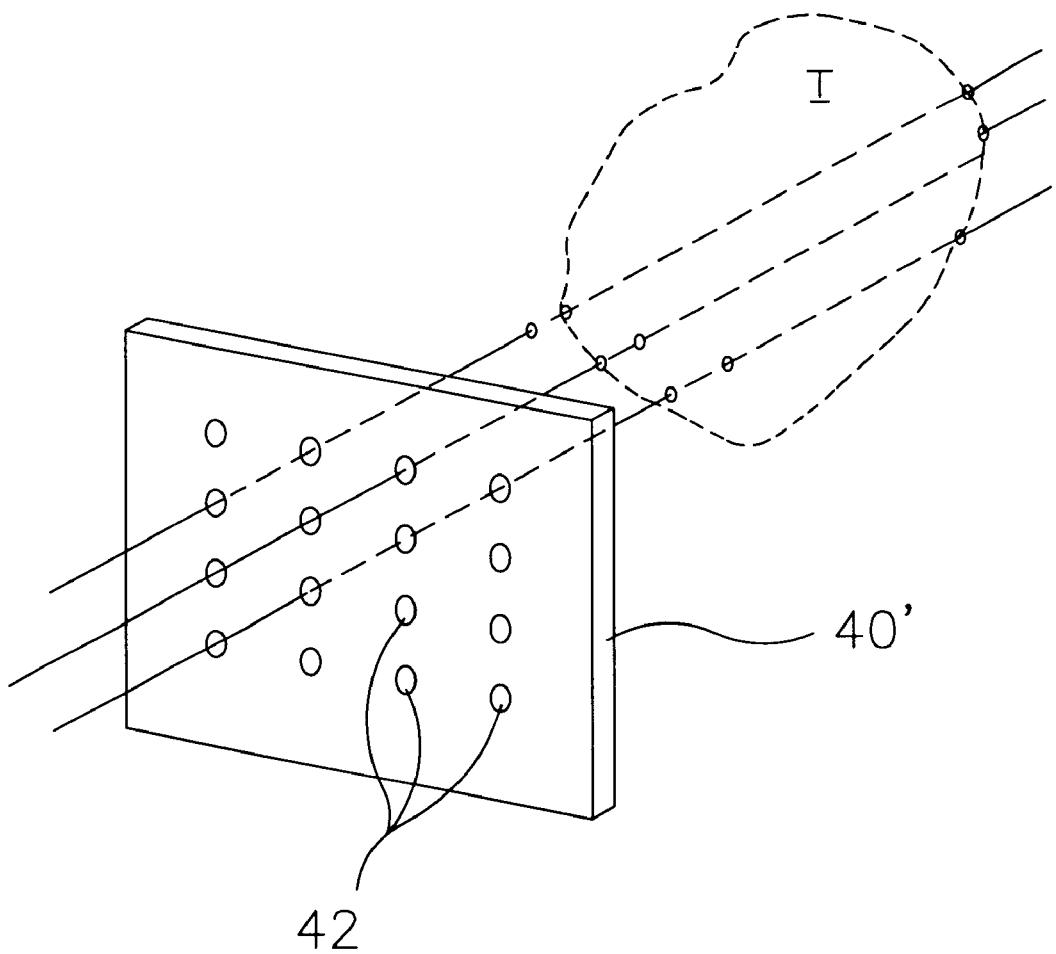
FIG. 8 is a schematic illustration of how a plurality of needles may be used to generate a 3-dimensional model of a tissue structure of interest.

FIG. 8 is a schematic view intended to illustrate another embodiment of a method of the invention used to generate more complex images. As noted above, each of the needle paths A—A through D—D in FIG. 6 are desirably generally parallel to one another. If each of these needle paths were aligned (e.g., if each of them fell within the plane of the paper in FIG. 6), this would; give the operator a set of data points generally defining the tissue structure along a given plane through that tissue. Such "tissue slice" information can be very useful in its own right, but it does not in and of itself allow a physician to visualize the tissue structure of interest in three dimensions. One of ordinary skill in the art will readily recognize, though, that providing a plurality of such "tissue slices" permits one to generate a 3-dimensional model of the tissue structure of interest without undue difficulty.

One of the problems in accurately depicting either a "tissue slice" image or a 3-dimensional image of the tissue structure is ensuring the reliability of the relative positions of the data points used to generate that image. If each needle path through the tissue structure is not known with some reasonable degree of certainty, the image which is generated will be somewhat unreliable.

The mechanism shown in FIG. 8 is intended to help arrange the needle paths in a predetermined relationship to ensure greater accuracy in rendering an image of the tumor T. In particular, a template 40' is provided with an array of guide ports 42 arranged in a predetermined relationship with respect to one another. Optimally, each of these guide ports 42 is adapted to fit fairly closely about the surface of the needle and extend some distance along the exterior of the needle to help guide the needle 50 along a fairly straight path. If the guide, ports 42 are too large or do not extend long enough along the needle, they will not ensure that the needle stays as close to the predetermined path as might be desired.

The template 40' of FIG. 8 can be used in a variety of ways. In one embodiment, the template is fixed in position with respect to the patient's tissue. A single needle 50 is then sequentially passed through a plurality of the guide ports 42 until an adequate image is obtained. Alternatively, a plurality of needles may be utilized, with each needle being passed through in a different guide port 42. Optimally, these needles are affixed to the template or a separate mounting block so that all of the needles can be advanced together as a single array. This arrangement allows one to relatively rapidly generate a 3-dimensional image of the structure of the patient's tissue and isolate a particular tissue structure of interest.

Much of the previous discussion focused on the use of one or more needles 50 to help generate an image or other understanding of the tissue mass through which the needle is advanced. This needle system 10 of the invention, therefore, represents a new type of diagnostic imaging tool available to a physician attempting to gain a better understanding of the structure of a particular tissue mass. Unlike many diagnostic imaging tools, though, the present invention is not limited to generating an image solely for informational purposes. Instead, the present invention permits the physician to actively manipulate and, if so desired, treat the tissue structure of interest.

One of the primary advantages of the present invention is that it gives the physician real-time feedback of the tissue structure through which the needle is passing. This information can permit the physician to perform a 'specified function on a tissue structure of interest with a greater degree of certainty that the needle is properly positioned when that function is performed.

In the case of a needle biopsy, for example, the needle 50 may be advanced through the patient's tissue while monitoring the strain signal until the strain signal indicates that the proximal margin of the tumor has been reached. At that point, the obturator within the needle may be retracted proximally and the needle 50 may be advanced a predetermined distance. Thereafter, the biopsy needle is typically twisted to sever the tissue in the needle from surrounding tissue and the needle can be retracted with the biopsied tissue in the lumen thereof.

In an alternative biopsy procedure, the needle has a closed distal tip and a window formed in a wall thereof. A cutting blade carried within the needle's lumen is formally positioned to cover that window during deployment of the needle. (Such biopsy needles are commonly used in the art and need not be discussed in detail here.) The needle will be advanced while monitoring the strain signal until the strain signal indicates that the proximal margin of the tumor has been reached. The needle may then be advanced at least the length of the window to position as much of the window as possible within the tumor. Alternatively, the needle may continue to be advanced while monitoring the strain signal until the strain signal indicates that the distal margin of the tumor has been reached, thereby pinpointing the proximal and distal margins of the tumor. The physician can then retract the needle proximally until the window is positioned at an optimum location within the tumor for the biopsy. The blade is then rotated to open the window, allowing adjacent tissue to spill into the lumen of the needle. Rotation of the cutting blade closes the window and severs a tissue sample and encloses it within the needle for retraction.

In other procedures, a needle 50 of the invention can allow the delivery of a particular therapeutic agent to the tissue structure of interest with a fairly high degree of precision. In the case of interstitial brachytherapy, for example, it is important to ensure that the radioactive seeds are positioned fairly precisely both with respect to the structure of the tumor and with respect to one another. As noted above, these radioactive seeds generally comprise at least one radioactive element with a relatively high energy emission level. Improper placement of these seeds can lead to unnecessary damage to healthy tissue and variable radiation dose to the body of the tumor.

Tracking the signal response curve of the needle as it moves through the patient's tissue will help the physician determine when the proximal margin of the tumor is reached. If so desired, the entire dose of radiation can be delivered after advancing the needle a further predetermined distance from that margin. Alternatively, the needle can continue to be advanced until the distal margin of the tumor is detected without depositing the radioactive seeds. Once the position of the proximal and distal margins of the tumor are noted, the needle can be carefully retracted and the radioactive seeds can be deposited after the needle is retracted proximally behind the distal margin of the tumor and before the distal tip of the needle reaches the proximal margin of the tumor.

A wide variety of other specialized techniques and adaptations may be appropriate for different types of interstitial brachytherapy or for other therapeutic procedures, but the exact nature of those particular techniques and/or implements is beyond the scope of the present disclosure. It should also be understood that the a nature of the therapeutic agent delivered through the needle 50 need not be limited to radioactive elements. Any of a variety of therapeutic drugs can be delivered in parenteral solutions, for example. It may even be possible to apply a therapeutic treatment to the tissue of interest without delivering any fluid or solid through a lumen of the needle. For example, the needle may be used to deliver ultrasound energy to a particular tissue structure, to selectively heat or cryogenically treat tissue, to treat the tissue with radio frequency or microwave energy, to apply laser or ultraviolet light to a tissue, or in high-dose radiation brachytherapy. In such a circumstance, it is entirely possible that the needle could be substantially solid, or at least have a closed distal end.

While a preferred embodiment of the present invention has been described, it should be understood that various changes, adaptations and modifications may be made therein without departing from the spirit of the invention and the scope of the appended claims.

What is claimed is:

1. A method of detecting at least one margin of a tissue structure of interest, comprising:
   a) providing a needle having a wall and a distal tip, a strain gage being connected to the needle wall at two spaced-apart locations, the strain gage generating a strain signal in response to strain on the wall of the needle;
   b) inserting the distal tip of the needle into a patient's tissue and advancing the needle distally into the tissue;
   c) monitoring the strain signal generated during said distal advancement of the needle; and
   d) analyzing the strain signal to detect the margin of the tissue structure.

2. The method of claim 1 wherein the strain gage is positioned distally of a proximal end of the needle, at least a portion of the strain gage being positioned within the patient's tissue during at least part of said distal advancement of the needle.

3. The method of claim 1 wherein analyzing the strain signal comprises identifying at least one amplitude change in a signal response curve and correlating said amplitude change with a margin of the tissue structure.

4. The method of claim 1 wherein the needle is advanced distally in a predetermined, repeatable manner by a motor, thereby reducing anomalies in the strain signal attributable to variations in advancement of the needle.

5. The method of claim 1 further comprising delivering a therapeutic agent to the tissue structure, the therapeutic agent being delivered only after detecting at least one margin of the tissue structure to ensure that the agent is being delivered to the tissue structure.

6. The method of claim 5 wherein the needle further comprises a lumen, the therapeutic agent being delivered through the lumen of the needle.

7. The method of claim 5 wherein the tissue structure of interest comprises a tumor and the therapeutic agent comprises at least one radioactive element, the radioactive element being delivered through a lumen of the needle.

8. A bioresponsive needle system comprising:
 a) an elongated needle adapted to be inserted into a patient's tissue, the needle having a lumen and a wall;
 b) a strain gage connected to the wall at two spaced-apart locations, the strain gage generating a strain signal in response to strain on the wall of the needle; and
 c) a strain monitor operatively connected to the strain gage and adapted to provide a user with feedback regarding the strain on the wall.

9. The needle system of claim 8 wherein the lumen of the needle extends distally to a distal tip of the needle, the distal tip of the needle being provided with a leading edge sufficiently sharp to penetrate a patient's tissue.

10. The needle system of claim 8 wherein the needle has a proximal end, a distal tip, and a body extending between the proximal end and the distal tip, a distal length of the body being adapted to be inserted into a patient's tissue, the strain gage being positioned along said distal length of the body.

11. The needle system of claim 10 further comprising a signal lead connected adjacent one end to the strain gage and extending proximally from the strain gage toward the proximal end.

12. The needle system of claim 10 wherein the strain gage is positioned proximally of the distal tip of the needle.

13. The needle system of claim 8 wherein the strain gage is positioned within the lumen of the needle.

14. The needle system of claim 8 wherein strain gage is positioned externally of the lumen of the needle.

15. The needle system of claim 14 wherein the needle system further comprises an external sheath extending along at least a portion of the length of the needle, the strain gage being positioned between the external sheath and an external surface of the wall.

16. The needle system of claim 8 further comprising a motor operatively connected to the needle proximally of a distal end thereof, the motor advancing the needle distally at a predetermined rate.

17. The needle system of claim 8 further comprising a motor connected to the needle proximally of a distal end thereof, the motor advancing the needle distally by applying a predetermined force.

18. The needle system of claim 8 wherein a plurality of said strain gages are connected to the wall.

* * * * *